United States Patent [19]
Llacer

[11] Patent Number: 5,602,892
[45] Date of Patent: Feb. 11, 1997

[54] METHOD FOR OPTIMIZATION OF RADIATION THERAPY PLANNING

[76] Inventor: Jorge Llacer, 130 Foret Hill Dr., Los Gatos, Calif. 95032

[21] Appl. No.: 619,305

[22] Filed: Mar. 21, 1996

[51] Int. Cl.$^6$ ........................................... A61N 5/10
[52] U.S. Cl. ............................. 378/65; 36/413.26
[58] Field of Search .................. 364/413, 26; 378/65

[56] References Cited

U.S. PATENT DOCUMENTS

| | | | |
|---|---|---|---|
| 3,987,281 | 10/1976 | Hodes | 235/151.3 |
| 5,205,289 | 4/1993 | Hardy et al. | 128/653.1 |
| 5,317,616 | 5/1994 | Swerdloff et al. | 378/65 |
| 5,351,280 | 9/1994 | Swerdloff et al. | 378/65 |
| 5,373,844 | 12/1994 | Smith et al. | 128/653.1 |
| 5,418,827 | 5/1995 | Deasy et al. | 378/65 |
| 5,528,650 | 6/1996 | Swerdloff et al. | 378/65 |

OTHER PUBLICATIONS

Starkschall 1984 A constrained least–squares optimization method for external beam radiation therapy treatment planning Med. Phys. 11 (5) pp. 659–665.
Powlis, et al. 1988 Semi–automated radiotherapy treatment planning with a mathematical mediator satisfy treatment goals Int. Rad. Oncology Biol. Phys. vol. 16 pp. 271–276.
Bortfeld et al. 1993 Optimization of beam orientations in radiation therapy same theoretical consideration Phys. Med. Biol. 38, pp. 291–304.
Gustafsson 1994 A generalized pencil beam algorithm for optimizing of radiation therapy Med. Phys. 21 (3) pp. 343–356.
Holmes et al. 1994 An iterative filtered backprojection inverse treatment planning algorithm for therapy Int. J. Rad. Oncology Biol. Phys. vol. 32 pp. 1215–1225.
Yuan et al. 1994 Application of Bayesian and Maximum Entrophy Optimisation to Conformation Radiotherapy Treatment Planning Applied Sig. Process, 1:20–34.
Sandham et al. 1995 Conformal Therapy using maximum entropy optimizing Int.J. Imag.Systems and Tech, 6 pp. 80–90.
Webb 1995 Optimizing Radiation Therapy Inverse Treatment Planning Using the Simulator Annealing Technique Int. J. Imag.Systems and Tech., 6, pp. 71–79.
Bortfeld et al. 1995 The exponential Radon transform and rejection filtering in radiotherapy planning Int.J.Imag.Systems and Tech. 6 pp. 62–70.

*Primary Examiner*—David P. Porta
*Assistant Examiner*—David Vernon Bruce

[57] ABSTRACT

A method for optimization of radiation therapy planning based on a new Dynamically Penalized Likelihood (DLP) algorithm. The target function of the DLP algorithm contains likelihood terms and penalty terms connected to the likelihood terms by a number of dynamically updated penalty coefficients. The method results in a highly uniform dose to the tumor or radiosurgery volume, at the expense of some non-uniformity in the dose delivered to defined sensitive tissues.

16 Claims, 6 Drawing Sheets

METHOD FOR OPTIMIZATION OF RADIATION THERAPY PLANNING

BACKGROUND OF THE INVENTION

1. Field of the Invention

The present invention relates generally to radiation therapy planning for the treatment of tumors or for stereotactic radiosurgery and more particularly to the optimization of the radiation dose delivered to a patient by inverse treatment planning.

2. Description of the Background Art

Medical equipment for radiation therapy treats tumorous tissues with high energy radiation. The dose and the placement of the dose must be accurately controlled to insure both that the tumor receives sufficient radiation to be destroyed, and that damage to the surrounding and adjacent non-tumorous tissue is minimized.

Internal-source radiation therapy places capsules of radioactive material inside the patient in proximity to the tumorous tissue. Dose and placement are accurately controlled by the physical positioning of the isotope. However, internal-source therapy has the disadvantages of any surgically invasive procedure, including discomfort to the patient and risk of infection.

External-source radiation therapy uses a radiation source that is external to the patient, typically either a radioisotope, such as $^{60}$Co, or a high-energy x-ray source, such as a linear accelerator. The external source produces a collimated beam directed into the patient to a treatment volume, which can be the tumor site or the site of radiosurgery. External-source radiation therapy avoids some of the problems of internal-source radiation therapy, but it undesirably and necessarily irradiates a significant volume of non-tumorous or healthy tissue in the path of the radiation beam along with the treatment volume.

The adverse effect of irradiating of healthy tissue may be reduced, while maintaining a given dose of radiation in the treatment volume, by projecting the external radiation beam into the patient at a variety of angles around a fixed axis, with the beams converging on the tumor site. The particular volume elements of healthy tissue, along the path of the radiation beam, are changed, reducing the total dose to each such element of healthy tissue during the entire treatment. The irradiation angles around the fixed axis are called gantry angles, since a gantry holding the radiation source and associated beam-delivery equipment rotates around the fixed axis.

As part of collimating the beam to the outline of the tumor, two offset angle of the radiation beam, with respect to a radius line between the radiation source and the center of rotation of the radiation source, may be adjusted to allow the treated volume to be other than at the center of rotation. The set of pencil beams thus created form a cone beam in three dimensions that can irradiate the complete treatment volume for each gantry angle. Changing the offset angles and the fluence for each of the pencil beams simultaneously allows treatment volumes having irregular cross-section within planes parallel to the plane of the gantry to be accurately targeted and radiation doses to healthy tissues to be minimized.

The objective of modern radiation therapy planning is to provide the values of a set of beam-delivery parameters that should be used in irradiating the treatment volume with adherence to a prescribed dose, while limiting the irradiation of healthy tissues to tolerable prescribed doses, lower than the dose to the treatment volume. Beam-delivery parameters may include gantry angles, the pencil beam offset angles within each selected gantry angle, and the fluence for each selected pencil beam.

The solution to the treatment planning problem is normally carried out as a direct problem: given a known set of beam characteristics and an initial estimate of the beam-delivery parameters, the dose deposited in a particular patient's tissues is calculated. This calculation can be made with accuracy in radiation treatment installations, using commercially-available computer programs or programs developed at the particular installation. If the dose distribution resulting from the initial estimate of the beam-delivery parameters satisfies the therapist's prescription reasonably well, it is then refined by trial-and-error. Although specific direct calculations can be very accurate, there is no assurance that the process will arrive at optimum beam-delivery parameters because of the trial-and-error nature of their selection.

The conformal treatment planning problem is an inverse problem in the sense that it inverts the calculation of dose distribution: Given a set of required doses, data on the patient's anatomy and the characteristics of all the available pencil beams, it calculates the beam-delivery parameters that best approximate the required doses. Of foremost importance in the inverse problem is the definition of the criterion that determines optimality. Current art can be summarized as either:

a) minimizing the sum of the squares of the errors between the dose desired in each volume element of the treatment volume and of sensitive tissues in the beam paths and the dose that would be delivered by the treatment plan (see G. Starkschall, "A constrained least-squares optimization method for external beam radiation therapy treatment planning", Med. Phys. 11 (5), pp. 659–665, 1984; T. W. Holmes, T. R. Mackie and P. Rechwerdt, "An iterative filtered backprojection inverse treatment planning algorithm for tomotheraphy", Int. J. Radiation Oncology, Physc., Vol. 32, No. 4, pp. 1215–1225, 1995; T. Borfeld and A. L. Boyer, "The exponential Radon transform and projection filtering in radiotheraphy planning", Int. J. Imaging Systems and Technology, Vol. 6, pp. 62–70, 1995; A. Gustafsson, B. K. Lind and A. Brahme, "A generalized pencil beams algorithm for optimization of radiation therapy", Med. Phys. 21 (3) pp. 343–356, 1994; T. Borfeld and W. Schlegel, "Optimization of beam orientations in radiation therapy: some theoretical considerations", Phys. Med. Bio. 38, pp. 291–304, 1993; U.S. Pat. No. 5,317,616 S. Swerdloff, T. R. Mackie and T. Holmes, "Method and apparatus for radiation therapy", May 31, 1994), or b) minimizing some cost functions which are functions of the same errors indicated in a) (see S. Webb, "Optimizing radiation therapy inverse treatment planning using the simulated annealing technique", Int. J. Imaging Systems and Technology, Vol. 6, pp. 71–79, 1995), or c) maximizing the smoothness of the dose distributions in the treatment volume and in the sensitive tissues while keeping the actual delivered doses near the prescribed doses (see W. A. Sandham, Y. Yuan and T. S. Durrani, "conformal therapy using maximum entropy optimization", Int. J. Imaging Systems and Technology, Vol. 6, pp. 80–90, 1995), or d) solving a "feasibility" problem which results in a solution that satisfies some prescribed upper and/or lower bounds for the doses in the treatment volume and sensitive tissues (see W. D. Powlis, M. D. Altschuler, Y. Censor and E. L. Buhler, "Semi-automated radiotheraphy treatment planning with a mathematical model to satisfy treatment goals", Int. J. Radiation Oncology, Biol. Phys., Vol. 16, pp. 271–276, 1989), or e) proposing the use of a method for solving a set of optimization functions, but not describing the behavior of the solutions in the presence of inconsistencies in the data (see U.S. Pat. No. 5,418,827, J. O. Deasy and R. De Leone, "Method for radiation therapy planning", May 23, 1995; U.S. Pat. No. 4,373,844, V. Smith and R. A. Stone, "Inverse treatment planning method and apparatus for stereotactic radiosurgery", Dec. 19, 1994; U.S. Pat. No. 5,205,289, T. L. Hardy, G. W. Glover, L. D. Breynildson, "Three-dimensional computer graphics simulation and computerized numerical optimization for dose delivery and treatment planning", Apr. 17, 1993; U.S. Patent 3,987,281, L. Hodes, "Method of radiation therapy treatment planning", Oct. 19, 1976), or f) using the algebraic reconstruction technique (ART) to find the optimum set of beam fluences with minimum norm (see Y. Yuan, W. A. Sandham, T. S. Durrani, J. A. Mills and C. Deehan, "Application of Bayesian and maximum entropy optimisation to conformation radiotherapy treatment planning", Applied Sig. Process, 1, pp. 20–34, 1994.

All the above methods suffer from the fact that the laws that govern the loss of energy and dose deposition of photons (γ- or x-rays) in matter are fixed and the doses or bounds prescribed by a therapist for the treatment volume and for the sensitive tissues based on medical knowledge will, in general, be inconsistent with one another from the point of view of the physical laws. As a consequence of that inconsistency, attempts by any of the above methods to yield a therapy plan that tries to satisfy all the specified doses will result in a more irregular dose to the treatment volume than desirable and, in some cases, lead to meaningless solutions. Irregularity in the dose delivered to the treatment volume may result in under-irradiation of some parts of a tumor, for example, which lowers the probability of tumor control.

SUMMARY OF THE INVENTION

The present invention is a method for computing a treatment plan that results in an optimized dose distribution in the treatment volume while limiting the dose to defined sensitive tissues to a value which is only approximately equal to the prescription. The present method will insure a most uniform dose to the treatment volume at the expense of some deviations from the prescribed dose to the sensitive tissues in a way that is consistent with the laws of energy loss and dose deposition of photons. The nature of the deviations from the prescribed dose to the sensitive tissues is described by the following: some voxels (volume elements) of the sensitive tissues may receive a few-percent higher dose than prescribed while the rest of the voxels will receive a dose which is below the prescribed dose. The uniformity of dose delivered to sensitive tissues is not important in therapy planning, but the maximum value is.

Specifically the invention includes a method and apparatus for solving a numerical optimization problem that yields the pencil beam fluences that will result in the optimum treatment plan using a predetermined set of gantry angles and a set of selected pencil beams for each of those gantry angles.

The preferred method and apparatus for solving the numerical optimization problem comprises a computer running a new Dynamically Penalized Likelihood (DPL) iterative algorithm. Taking into consideration the desired doses in the treatment volume and sensitive tissues and the energy deposited per unit fluence into the patient's tissues by all the selected pencil beams of the predetermined gantry angles, the new DPL algorithm finds the beam fluences that maximize the target function:

$$B(a) = \sum_{i \in D} \left[ -\sum_j f_{ij} a_j + d_i \log \left( \sum_j F_{ij} a_j \right) - \log(d_i!) \right] - \sum_{i \in S} \beta_i \left( \sum_j f_{ij} a_j - s_i \right)^2$$

wherein:
 a=vector of pencil beam fluences
 j=index for each pencil beam
 $a_j$=fluence of a specific pencil beam
 i=index for each voxel (volume element) in the patient anatomy
 D=region that includes all treatment volume voxels
 $d_i$=dose desired in a specific treatment volume voxel
 S=region that includes all sensitive tissue voxels
 $s_i$=dose desired in a specific voxel of a sensitive tissue
 $F_{ij}$=matrix element that defines the dose delivered by pencil beam j to patient voxel i per unit fluence of the beam
 $\beta_i$=Penalization parameter for voxel i in the patient anatomy.

Maximization of the terms in the first summation (over region D) constitutes a Maximum Likelihood Estimator (MLE), an iterative process whose application to the treatment planning problem is one of the novelties of the DLP algorithm. The MLE yields a robust, well-behaved, non-negative solution with assured converge to a unique maximum. The terms in the second summation (over region S) are penalty terms imposed on the MLE when the MLE solutions result in doses to the sensitive tissues that are different from the desired ones. The use of penalty terms constitute another novelty in treatment planning. Parameters $\beta_i$ play a leading role in the dynamic character of the new algorithm. They control the degree of penalty suffered by the MLE solution during the iterative process in the following manner: a) as long as the dose delivered to a voxel i in the sensitive tissues is larger than the desired dose, $\beta_i$ increases with each iteration in order to decrease the fluxes assigned to the beams that traverse pixel i. The rate of increase is proportional to the positive difference between the dose delivered and the desired dose for voxel i at each iteration. If that difference becomes zero or negative for a specific voxel, the rate of increase of the corresponding $\beta_i$ goes to zero.

An alternative method and apparatus for solving the numerical optimization problem comprises a computer running a computer code that maximizes the likelihood terms of the preferred method, and having penalty terms which are a function of $$\sum_j F_{ij} a_j - s_i$$

different from the quadratic function of the preferred method.

Another alternative method and apparatus for solving the numerical optimization problem is a computer running a computer code that maximizes the likelihood terms of the preferred method, and having penalty terms whose parameters $\beta_i$ are initialized before starting the iterative procedure and are updated by a schedule different from the one of the preferred method.

A primary object of the present invention is to provide optimization of dose delivery in various radiation treatments, such as tumor therapy or radiosurgery.

Another object of the invention is to match radiation doses in the treatment volume to the desired dose in that volume.

Another object of the invention is to provide acceptably low doses to sensitive tissues in the path of the radiation beams.

An advantage of this invention is that the radiation dose delivered to the treatment volume is of high uniformity at the expense of uniformity in the dose delivered to the sensitive tissues, where uniformity is not as important as in the treatment volume.

Another advantage of this invention is that the calculation of the treatment plan is stable and converges uniformly to a final result, without algorithm parameters to be adjusted by the user.

Yet another advantage of this invention is that it will yield useful solutions in difficult therapy situations, as in the case of a tumor surrounded by a large volume of sensitive tissues, where methods will fail.

Other objects, advantages and novel features will be set forth in part in the following portions of the specification, wherein the detailed description is for the purpose of fully disclosing the preferred embodiment of the invention, without placing limitations thereon.

BRIEF DESCRIPTION OF THE DRAWINGS

The accompanying drawings, which are incorporated into and form a part of the specification, illustrate the preferred embodiment of the invention and, together with the description, serve to explain the principles of the invention. The drawings are only to illustrate the preferred embodiment of the invention and are not to be construed as limiting the invention.

DESCRIPTION OF THE PREFERRED EMBODIMENT

Figure 1:
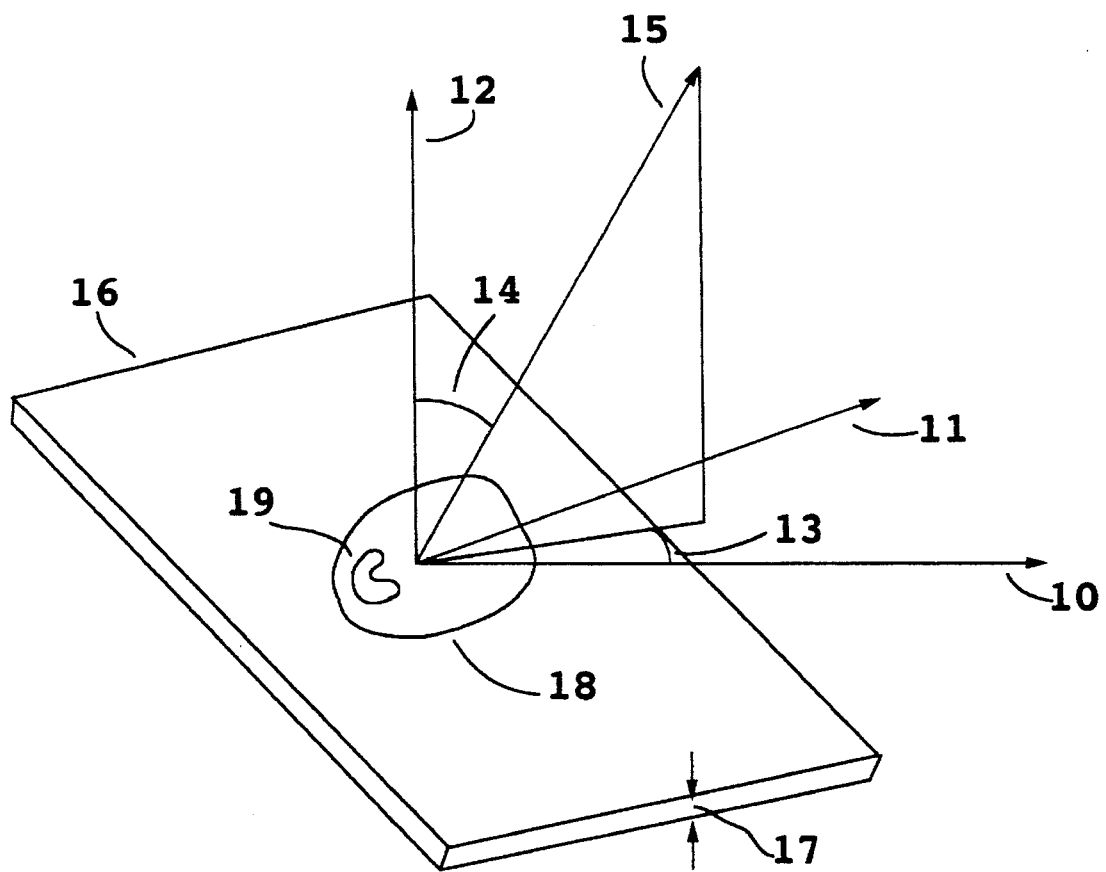
FIG. 1 is a perspective view of the environment and coordinate systems in which the present invention can be used.

Referring to FIG. 1, the environment of the present invention is shown as a set of three orthogonal coordinate axes 10, 11, and 12 which are fixed in the therapy room and are used as reference for positioning equipment, a patient, etc. Two angles 13 and 14 define a therapy orientation vector 15 which is perpendicular to a plane 16 of thickness 17. Usually, a contiguous stack of planes 16 will be defined to include the totality of the section of patient anatomy that includes a treatment volume. Only one of the planes 16 is shown. A closed line 18 describes the outline of the intersection of plane 16 with the patient's body. A closed line 19 describes the outline of the intersection of plane 16 with the treatment volume. Vector 15, and consequently the orientation of plane 16 with respect to axes 10, 11, and 12, is selected by the therapist as the therapy orientation vector that is expected to lead to the most favorable treatment. The treatment plan for a specific patient may consist of more than one vector 15. For the description that follows, only one plane 16 corresponding to one vector 15 will be considered. The extension to a stack of planes or to several stacks of planes would be immediately understandable to a practicioner in the area of radiation therapy planning.

Figure 2:
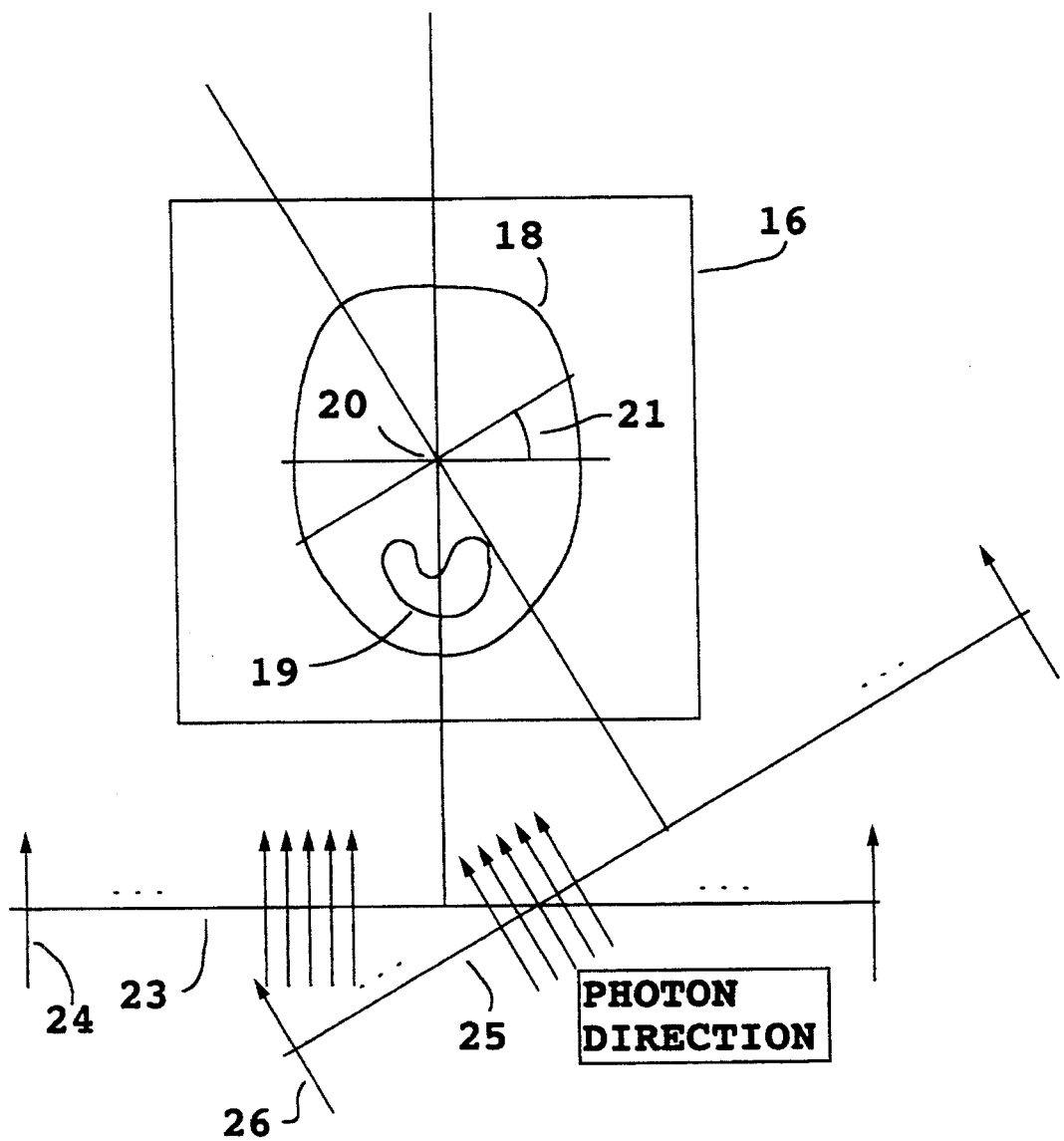
FIG. 2 is a view of the environment in which the present invention can be used seen from a point on the axis of a rotating gantry.

FIG. 2 is a view of plane 16 from a point in vector 16. Vector 15 crosses plane 16 perpendicularly at the center 20, out of the paper, towards the reader. Plane 16 is the plane of the therapy gantry, which rotates about vector 15, i.e., about the center 20. The view of FIG. 2 will be used to describe the present invention. The therapy gantry contains a source of photons that can generate pencil beams that spread as a cone towards the treatment volume, or it can generate a large number of parallel pencil beams for each angle of the gantry. The description of this invention can be made in terms of either spreading or parallel beams without changing its nature. A group of pencil beams corresponding to a single gantry angle is called a port, independently of whether the beams are spreading or are parallel. The description of this invention will use the definition of a port as a group of parallel pencil beams belonging to a gantry angle. Angle 21 defines a port. The port for angle 21 being zero degrees is shown by a line 23, containing a large number of parallel pencil beams 24. The port for angle 21 being approximately 30 degrees is shown by a line 25, containing a large number of parallel pencil beams 26. Only a few of the pencil beams 24 and 26, are shown. It is considered that there are a number N of evenly spaced possible ports with corresponding angles 21 spanning from 0 to 360 degrees.

I. The Selection of Optimum Ports

Figure 3:
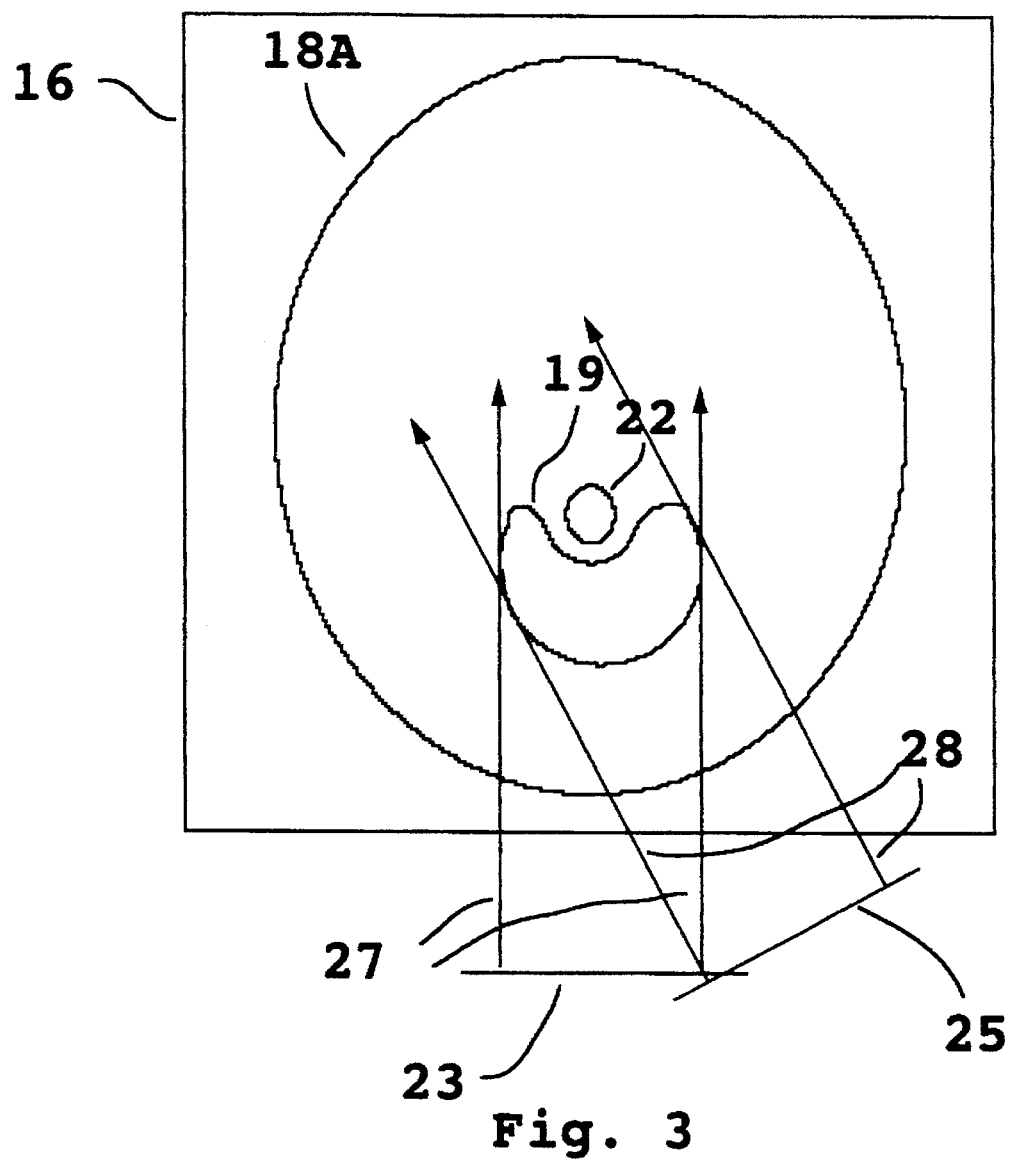
FIG. 3 is a line drawing showing outlines of a hypothetical brain, of a tumor and of sensitive tissues for an illustrative problem.

FIG. 3 shows a computer generated precise description of plane 16, the outline of a hypothetical elliptical head 18A just above the eye level, the outline of a tumor 19 and the outline of sensitive tissues 22. The elements of FIG. 3 define an illustrative problem that will facilitate the comprehension of this invention.

This invention assumes that, based on previous medical experience, available therapy time, cost, logistic considerations and/or mathematical analysis of the specific case, the therapist will define the number of ports $N_p$ that will be used for the treatment of a specific patient, with $N_p < N$. Likewise, this invention assumes that the choice of which specific ports will form the optimal set of $N_p$ ports, out of the possible N ports, will also be made by the therapist. Once the set of optimum ports has been chosen, a set of active beams can be defined. Active beams are those beams that traverse the treatment volume and will, therefore, be used in the therapy planning for the specific patient. This selection can be done by any of the techniques that are in common use in therapy planning. FIG. 3 shows the extreme left and right active beams 27 for port 23 and the extreme left and right active beams 28 for port 25. The totality of active beams for all the chosen optimal set of $N_p$ ports will form the set of active beams. This invention does not provide a method for selecting the active beams.

II. Calculation of Dose Matrix F

The dose matrix F has elements $F_{ij}$ which correspond to the dose per unit fluence delivered by therapy beam j to voxel i in the patient's anatomy. The calculation of the matrix elements can be done either in a fast approximate method for the purposes of demonstration or preliminary assessment of a therapy situation, or using a slower, accurate computer code that takes into consideration all the mechanisms of photon energy loss in matter. Radiation therapy institutions have developed or purchased computer codes that are available for both the approximate and accurate calculations. The present invention does not provide a method for calculation of the dose matrix F, but makes the following observations:

a) It is only necessary to calculate the elements $F_{ij}$ that correspond to the active beams.

and b) The matrix is sparse and sparse techniques for storage can be used to reduce its size in the computer.

III. Numerical Optimization Algorithm

The preferred numerical optimization algorithm of the present invention starts from a description of the active beams that are going to be used in a specific therapy planning calculation as discussed in I, from a knowledge of the matrix F calculated as discussed in II and the desired dose distributions for therapy volume and for the sensitive tissues. For the illustrative example, the therapy volume is tumor 19 and sensitive tissues are described as sensitive tissues 22. The Dynamically Penalized Likelihood (DLP) target function to be maximized is $$B(a) = \sum_{i \in D} \left[ -\sum_j f_{ij} a_j + d_i \log \left( \sum_j F_{ij} a_j \right) - \log(d_i!) \right] - \sum_{i \in S} \beta_i \left( \sum_j f_{ij} a_j - s_i \right)^2$$

wherein:

a=vector of active beam fluences j=index for each active beam $a_j$=fluence of a specific active beam i=index for each voxel (volume element) in the patient anatomy D=region that includes all treatment volume voxels $d_i$=dose desired in a specific treatment volume voxel S=region that includes all sensitive tissue voxels $s_i$=dose desired in a specific voxel of a sensitive tissue $F_{ij}$=matrix element that defines the dose delivered by active beam j to patient voxel i per unit fluence of the beam.

$\beta_i$=penalization parameter for voxel i in the patient anatomy

The preferred method for maximizing the target function B(a) is by using the iteration formula:

$$a_j^{(k+1)} = a_j^{(k)} \frac{C}{q_j} \left[ \sum_{i \in D} F_{ij} \frac{d_i}{h_i^{(k)}} - \sum_{i \in S} \beta_i F_{ij} (h_i^{(k)} - s_i) \right]^n$$

wherein:

the superscript (k) indicates the results of the $k^{th}$ iteration, $h_i^{(k)} = \sum F_{ij} a_j^{(k)}$ is the projection of fluences after the kth iteration onto the dose plane 16, $$q_j = \sum_{i \in D} F_{ij},$$

C is a normalization constant that is used to require that $$\sum_j a_j^{(k+1)} = \sum_j a_j^{(k)}$$

after each iteration, and n is an exponent that can be used to accelerate convergence.

The first summation within the brackets corresponds to the likelihood terms, while the second summation corresponds to the dynamic penalization terms. The iterative formula can be derived from the target function B(a) by the successive substitution method, described in the literature of tomographic medical and astronomical image reconstruction. Other methods for maximization of the target function B(a) exist as, for example, the Expectation Maximization algorithm, gradient descent methods, Algebraic Reconstruction Technique (ART) and related, and simulated annealing.

Figure 4:
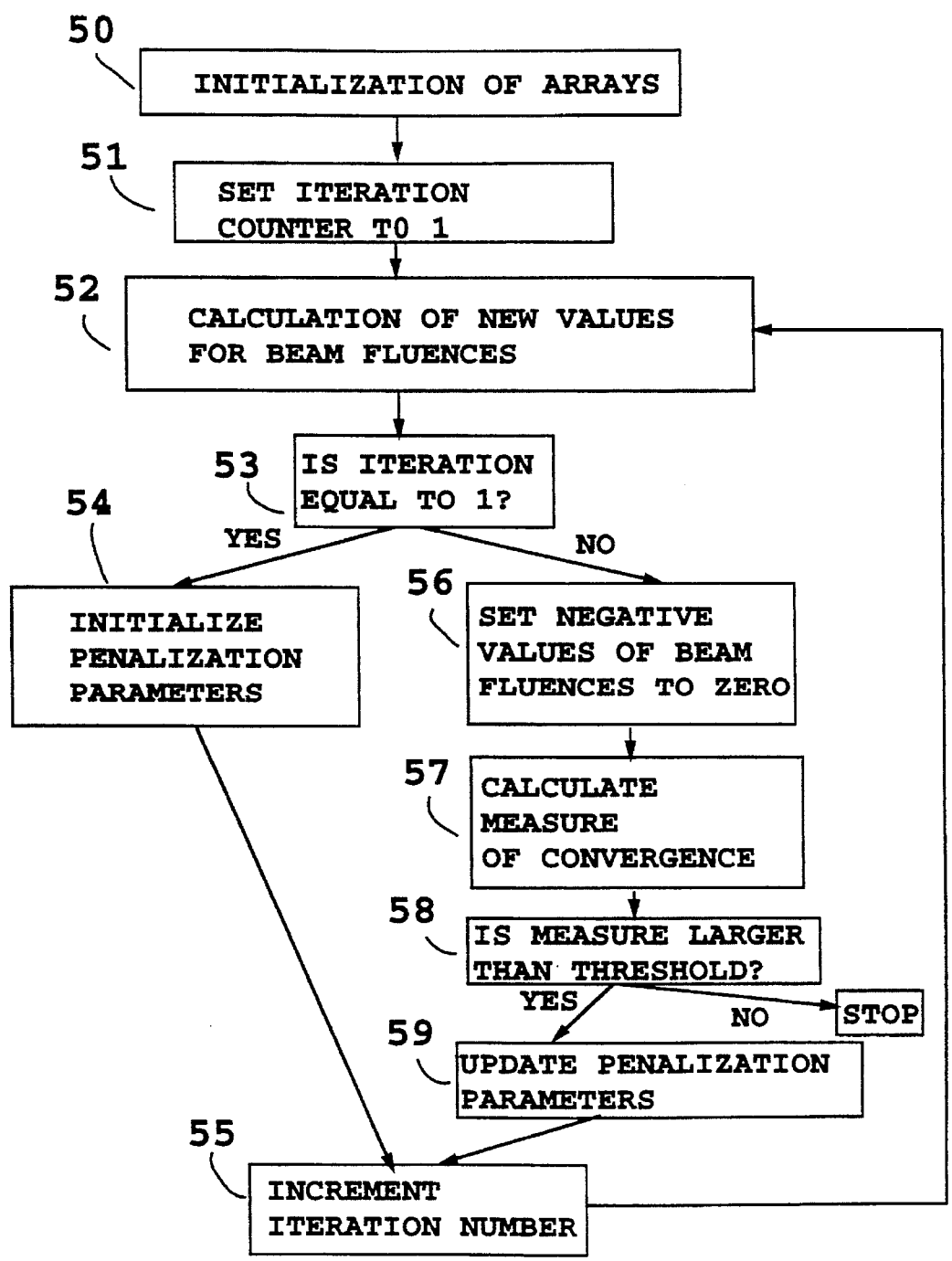
FIG. 4 is a flow diagram for the preferred process of optimization of the beam fluences using the dynamically penalized likelihood method.

With reference to FIG. 4, before the iterative procedure starts, the initialization of arrays takes place at step 50: variables $a_j$ are set equal to unity, all values of the penalization parameters $\beta_i$ are set equal to zero and the desired doses $d_i$ and $s_i$ are set to their values. The iterative procedure is then started at step 51 by setting the iteration counter k equal to 1. The calculation of new values for active-beam fluences $a_j$ is then carried at step 52 by using the iteration formula that maximizes the target function B(a). A test for iteration number is done at step 53. If the iteration counter is equal to 1, the initialization of the dynamic penalization parameters $\beta_i$ is done, step 54, by setting:

$$\beta_i^{(initial)} = \frac{N_\lambda}{\sum_{j, \lambda_j > 0} \frac{\lambda_j}{K q_j}}, i \in S$$

wherein:

K is a constant that controls the speed of the dynamic process, $$\lambda_j = \sum_{i \in S} F_{ij} (h_{iL}(k) - s_i),$$

and $N_\lambda$ is the number of values of $\lambda_j$ that are positive.

The value of K has to be smaller than unity, but is not critical within a range of 0.01 to 0.2. A value of K=0.1 has been established as a useful one.

Iteration 1 has then been completed and the process increments the iteration counter by 1 at step 55. For iteration 2 and succeeding iterations, the process returns to calculating new values for beam fluences $a_j$ at step 52. Since iteration counter is no longer one, the process branches to step 56 to check whether any values of active-beam fluences $a_j$ have become negative. Those that have become negative are set equal to zero. At step 57 the algorithm calculates a measure of convergence with the purpose of deciding whether the iterative process can be terminated. One such measure is the root mean square error (rms) between delivered doses in the treatment volume and the desired doses:

$$rms = \left[ \sum_{i \in D} (h_i^{(k)} - d_i)^2 \right]^{1/2}$$

A test is done at step 58: if the rms error is less then some predetermined threshold value, the algorithm stops. Otherwise an update of the previous values of the penalization parameters $\beta_i$ is carried out at step 59 by the formula:

$$\beta_i^{(new)} = \beta_i^{(old)} + \beta_i^{(initial)} \frac{h_i^{(k)} - s_i}{s_i} \quad , i \in S, \; h_i^{(k)} - s_i > 0, \; s_i > 0$$

The updating of step 59 changes the rate of increase of the parameters $\beta_i$ with each iteration proportionally to the positive difference between the dose delivered to voxels in the sensitive tissues and the desired dose for those voxels. If the difference is zero or negative, the corresponding $\beta_i$ parameter is not changed. After the updating step 59 the iteration number is incremented at step 55 and a new iteration starts.

Figure 5:
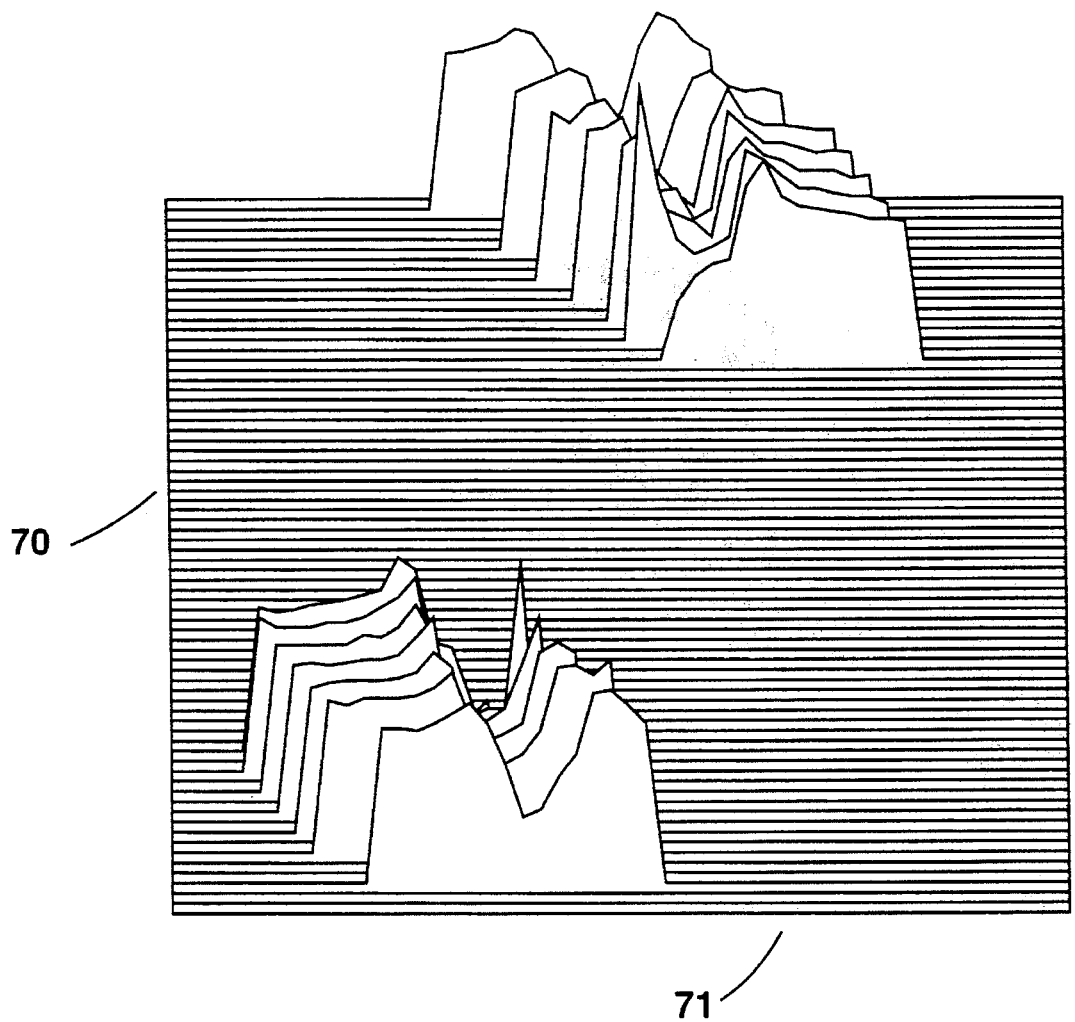
FIG. 5 is a contour plot of the beam fluences resulting from the optimization of the illustrative example, using the preferred method of optimization. The elevation corresponds to the fluence desired for each pencil beams of the 14 ports of the example.

When the iterative process is stopped by achieving a predetermined minimum measure of error, the values of $a_j$ obtained in the last iteration are the optimized fluences for the active beams. FIG. 5 shows a contour plot of resulting fluences for the illustrative example with the number of arbitrarily selected ports $N_p=14$. Axis 70 corresponds to the port number while axis 71 corresponds to the active beam number in each port. The elevation corresponds to the fluence for each of the active beams of the selected ports. The desired doses for the example were 100 arbitrary units for tumor 19 and 40 units for sensitive tissues 22.

Figure 6:
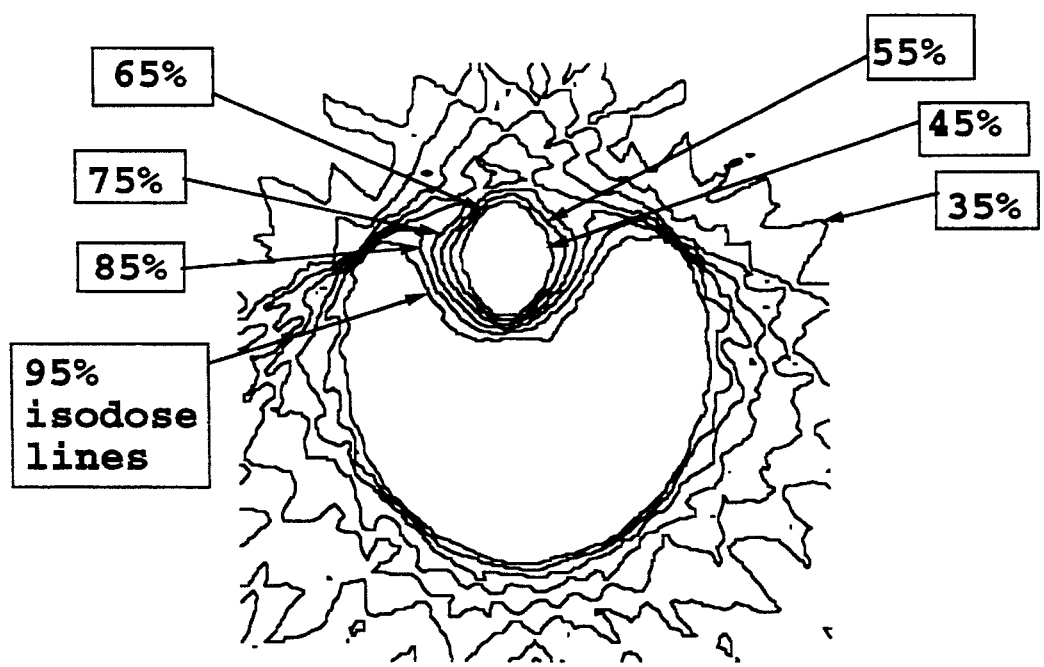
FIG. 6 is a plot of isodose lines (lines of equal dose) for the doses delivered to the hypothetial patient of the illustrative example, using the preferred method of opimization.

FIG. 6 shows isodose lines (lines of equal dose) on the region of tumor 19 and sensitive tissues 22 that would result from applying the optimized fluences of FIG. 5. The area of tumor 19 is well contained within the 95% isodose line and the area of the sensitive tissues 22 is well contained within the 45% isodose line. The rms error in area of tumor 19 is less than 0.9%. The doses to the sensitive tissues 22 range from 37.89% to 44.6%, with the majority of voxels under the prescribed 40%. The results shown correspond to 50 iterations of the DPL algorithm, which are estimated to require approximately a total of 35 seconds in a Hewlett Packard 735 computer. The illustrative example was set up in a 256×256 array of voxels for plane 16. The dose matrix F was calculated by a fast approximate method, as discussed in II.

I claim:

1. An improved method of inverse radiation treatment planning enabling the production and display of a desirable radiation dose distribution from a predetermined number and arrangement of active beams, said method comprising the steps of:
   a. calculating optimum fluences for said active beams by the process of maximization of a target function which includes a plurality of likelihood terms and a plurality of penalty terms linked by a plurality of penalization parameters, and
   b. modifying said penalization parameters during said process of maximization according to a schedule whose characteristics change dynamically as said process of maximization proceeds.

2. The method of treatment planning according to claim 1, wherein said step of calculating optimum fluences includes the maximization of a target function comprising a plurality of likelihood terms of the form:

$$-\sum_j F_{ij} a_j + d_i \log \left( \sum_j F_{ij} a_j \right)$$

wherein
j=index for each active beam,
$a_j$=fluence of a specific active beam,
i=index for each volume element (voxel) in the patient anatomy, $d_i$=dose desired in a specific voxel of the treatment volume,
$F_{ij}$=matrix element that defines the dose delivered by active beam j to patient voxel i per unit fluence of the beam.

3. The method of treatment planning according to claim 1, wherein said step of calculating optimum fluences includes the maximization of a target function comprising a plurality of penalty terms which are functions of an expression comprising the terms $$\sum_j F_{ij} a_j - s_i,$$

wherein $s_i$ is the dose desired in voxel i of sensitive tissues.

4. The method of treatment planning according to claim 3, wherein said functions are quadratics of the form:

$$\beta_i \left( \sum_j F_{ij} a_j - s_i \right)^2$$

wherein $\beta_i$ is the penalization parameter for voxel i in the patient anatomy.

5. The method of treatment planning according to claim 1, wherein said step of calculating optimum fluences by the process of maximization of a target function is carried out by an iterative formula comprising the expression:

$$a_j^{(k+1)} = a_j^{(k)} \frac{C}{q_j} \left[ \sum_{i \in D} F_{ij} \frac{d_i}{h_i^{(k)}} - \sum_{i \in S} \beta_i F_{ij} (h_i^{(k)} - s_i) \right]^n$$

wherein:
the superscript (k) indicates the results of the $k^{th}$ iteration, $$h_i^{(k)} = \sum_j F_{ij} a_j^{(k)}$$

$$q_j = \sum_{i \in D} F_{ij},$$

D=region that includes all treatment volume voxels,
S=region that includes all sensitive tissue voxels,
C is a normalization constant that is used to require that $$\sum_j a_j^{(k+1)} = \sum_j a_j^{(k)}$$

after each iteration,
and n is an exponent that can be used to accelerate convergence.

6. The method of treatment planning according to claim 1, wherein said step of modifying said penalization parameters includes the steps of:
   a) initializing the values of said penalization parameters in a predetermined way at the beginning of said process of maximization, and
   b) updating the values of said penalization parameters as a function of expressions comprising the terms $$\sum_j F_{ij} a_j - s_i$$

as said process of maximization proceeds.

7. The method of treatment planning according to claim 6 wherein said step of initializing the values of said penalization parameters is carried out by a formula comprising the expression:

$$\beta_i^{(initial)} = \frac{N_\lambda}{\sum_{j,\lambda_j>0} \frac{\lambda_j}{Kq_j}}, i \in S$$

wherein $\beta_i^{(initial)}$ is the initial value of the penalization parameter for voxel i in the patient anatomy, K is a constant smaller than unit, $$\lambda_j = \sum_{i \in S} F_{ij}(h_i^{(k)} - s_i)$$

after the first iteration and $N_\lambda$ is the number of values of $\lambda_j$ that are positive.

8. The method of treatment planning according to claim 6 wherein said step of updating the values of said penalization parameters is carried out by a formula comprising the expression:

$$\beta_i^{(new)} = \beta_i^{(old)} + \beta_i^{(initial)} \frac{h_i^{(k)} - s_i}{s_i}, i \in S, h_i^{(k)} - s_i > 0, s_i > 0,$$

wherein:

$\beta_i^{(new)}$ is the updated value of the penalization parameter for voxel i in the patient's anatomy, and $\beta_i^{(old)}$ is the value of the penalization parameter for voxel i in the patient's anatomy before updating.

9. An apparatus for optimizing the process of inverse radiation treatment planning enabling the production and display of a desirable radiation dose distribution from a predetermined number and arrangement of active beams, involving computer techniques comprising:

a. means for calculating optimum fluences for said active beams by the process of maximization of a target function which includes a plurality of likelihood terms and a plurality of penalty terms linked by a plurality of penalization parameters, and b. means for modifying said penalization parameters during said process of maximization according to a schedule whose characteristics change dynamically as said process of maximization proceeds.

10. The apparatus of claim 9, wherein said means for calculating optimum fluences includes means for the maximization of a target function comprising a plurality of likelihood terms of the form:

$$-\sum_j F_{ij}a_j + d_i \log\left(\sum_j F_{ij}a_j\right)$$

wherein j=index for each active beam, $a_j$=fluence of a specific active beam, i=index for each volume element (voxel) in the patient anatomy, $d_i$=dose desired in a specific voxel of the treatment volume, $F_{ij}$=matrix element that defines the dose delivered by active beam j to patient voxel i per unit fluence of the beam.

11. The means of claim 9, wherein said means for calculating optimum fluences includes means for the maximization of a target function comprising a plurality of penalty terms which are functions of an expression comprising the terms $$\sum_j F_{ij}a_j - s_i,$$

wherein $s_i$ is the dose desired in voxel i of sensitive tissues.

12. The means of claim 11, wherein said functions are quadratics of the form:

$$\beta_i \left(\sum_j F_{ij}a_j - s_i\right)^2$$

wherein $\beta_i$ is the penalization parameter for voxel i in the patient anatomy.

13. The means of claim 9, wherein said step of calculating optimum fluences by the process of maximization of a target function is carried out by an iterative formula comprising the expression:

$$a_j^{(k+1)} = a_j^{(k)} \frac{C}{q_j} \left[ \sum_{i \in D} F_{ij} \frac{d_i}{h_i^{(k)}} - \sum_{i \in S} \beta_i F_{ij}(h_i^{(k)} - s_i) \right]^n$$

wherein:

the superscript (k) indicates the results of the $k^{th}$ iteration, $$h_i^{(k)} = \sum_j F_{ij} a_j^{(k)}$$

$$q_j = \sum_{i \in D} F_{ij},$$

D=region that includes all treatment volume voxels,

S=region that includes all sensitive tissue voxels,

C is a normalization constant that is used to require that $$\sum_j a_j^{(k+1)} = \sum_j a_j^{(k)}$$

after each iteration, and n is an exponent that can be used to accelerate convergence.

14. The means of claim 9, wherein said step of modifying said penalization parameters includes the means for:

a) initializing the values of said penalization parameters in a predetermined way at the beginning of said process of maximization, and b) updating the values of said penalization parameters as a function an expression comprising the terms $F_{ij}a_j-s_i$ as said process of maximization proceeds.

15. The means of claim 14 wherein said step of initializing the values of said penalization parameters is carried out by a formula comprising the expression:

$$\beta_i^{(initial)} = \frac{N_\lambda}{\sum_{j,\lambda_j>0} \frac{\lambda_j}{Kq_j}}, i \in S$$

wherein $\beta_i^{(initial)}$ is the initial value of the penalization parameter for voxel i in the patient anatomy, K is a constant smaller than unity, $$\lambda_j = \sum_{i \in S} F_{ij}(h_i^{(k)} - s_i)$$

after the first iteration and $N_\lambda$ is the number of values of $\lambda_j$ that are positive.

16. The means of claim 14 wherein said step of updating the values of said penalization parameters is carried out by a formula comprising the expression:

$$\beta_i^{(new)} = \beta_i^{(old)} + \beta_i^{(initial)} \frac{h_i^{(k)} - s_i}{s_i}, i \in S, h_i^{(k)} - s_i > 0, s_i > 0,$$

wherein:

$\beta_i^{(new)}$ is the updated value of the penalization parameter for voxel i in the patient's anatomy, and $\beta_i^{(old)}$ is the value of the penalization parameter for voxel i in the patient's anatomy before updating.

* * * * *